United States Patent [19]

Dellacoletta et al.

[11] 4,410,735
[45] Oct. 18, 1983

[54] METHOD FOR MAKING BISPHENOXIDE SALTS

[75] Inventors: Brent A. Dellacoletta, Evansville, Ind.; John W. Verbicky, Scotia, N.Y.

[73] Assignee: General Electric Company, Schenectady, N.Y.

[21] Appl. No.: 325,878

[22] Filed: Nov. 30, 1981

[51] Int. Cl.³ .............................................. C07C 39/16
[52] U.S. Cl. ................................................... 568/722
[58] Field of Search ............... 568/723, 724, 730, 722; 528/126

[56] References Cited

U.S. PATENT DOCUMENTS

| | | | |
|---|---|---|---|
| 2,858,342 | 10/1958 | Bender et al. | 568/723 |
| 3,238,263 | 3/1966 | Schetelich et al. | 568/722 |
| 3,852,242 | 12/1974 | White | 568/723 |
| 3,960,968 | 6/1976 | Vernalekena et al. | 568/723 |
| 4,202,993 | 5/1980 | Takekoshi | 568/723 |
| 4,257,953 | 3/1981 | William et al. | 568/723 |
| 4,302,616 | 11/1981 | William et al. | 568/723 |

Primary Examiner—Werren B. Lone
Attorney, Agent, or Firm—William A. Teoli; James C. Davis, Jr.; James Magee, Jr.

[57] ABSTRACT

A process is provided for making bisphenoxide salts by the flash evaporation of water from an aqueous mixture of a bisphenol and an alkali metal hydroxide. Improved control over the stoichiometry of the bisphenol and the alkali metal hydroxide in the aqueous mixture is achieved by monitoring bisphenol content in the aqueous bisphenoxide salt mixture. An extractive organic solvent for the bisphenol is used with an aliquot of the bisphenoxide salt mixture. The stoichiometric balance in the aqueous bisphenoxide salt mixture is determined by measuring the absorbance value of the bisphenol in the organic solvent phase, and comparing it to a known curve obtained by plotting known bisphenol absorbance values and equivalents of alkali metal hydroxide.

6 Claims, 1 Drawing Figure

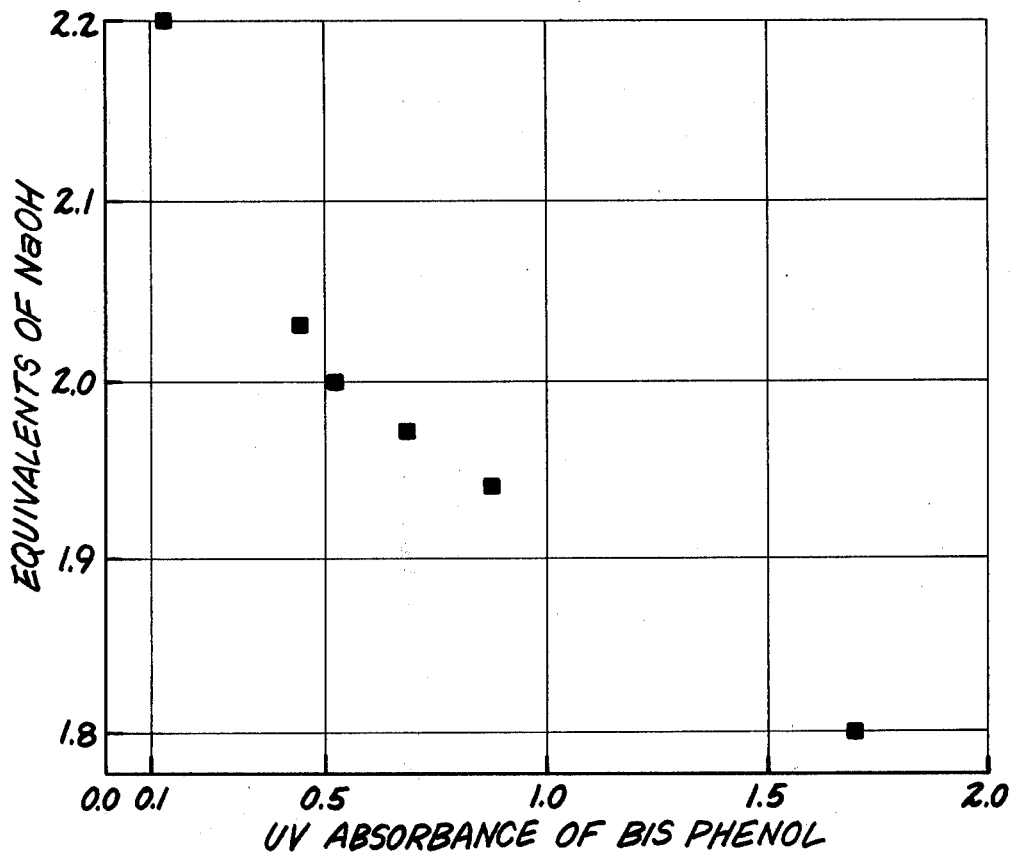

METHOD FOR MAKING BISPHENOXIDE SALTS

BACKGROUND OF THE INVENTION

Prior to the present invention, as shown by Takekoshi, U.S. Pat. No. 4,202,933, anhydrous alkali metal bisphenol salts were prepared by effecting the rapid separation of water from an aqueous mixture having stoichiometric quantities of sodium hydroxide and bisphenol. The bisphenol salt was then used to make aromatic ether bisimides or polyetherimides based on the nature of the nitro-, or halo-phthalimide used. For example, U.S. Pat. No. 3,852,242, assigned to the same assignee as the present invention, shows a method for making polyetherimides by effecting reaction between bisphenoxide salts and bis(nitrophthalimide). The bisphenoxide salts made by the procedure shown in U.S. Pat. No. 4,202,993 can also be used to make polyethersulfones, polycarbonates, polyesters, and epoxy derivatives.

Although the procedure shown by Takekoshi in U.S. Pat. No. 4,202,993 provides bisphenoxide salts which can be used to make a variety of valuable organic polymers, experience has shown that unless the stoichiometric relationship of the sodium hydroxide and the bisphenol is maintained with 1.5% (i.e., 1.97-2.03 equivalence of sodium hydroxide per equivalent of bisphenol), the usefulness of the bisphenoxide salts, that is the yield of the bisimide products obtained by nitro displacement reactions, for example, the reaction between the sodium salt of bisphenol-A and nitro-phthalimide to produce the corresponding aromatic bis(ether phthalimide) can be drastically reduced unless a stoichiometric relationship is maintained between the phenol and the alkali metal hydroxide in the aqueous phenoxide salt mixture. However, it has been found during the course of the manufacture of bisphenoxide salt by the aforementioned method of Takekoshi, the stoichiometric relationship of the alkali metal hydroxide and the bisphenol in the aqueous alkali metal bisphenoxide salt mixture can vary to produce problems with respect to the yield of the polyetherimide obtained by using such bisphenoxide salt.

The present invention is based on the discovery that the stoichiometry of the bisphenol and the alkali metal hydroxide can be monitored in the aqueous bisphenoxide salt mixture by contacting the aqueous bisphenoxide salt mixture with an organic solvent to effect extraction of a detectable amount of bisphenol from the aqueous salt mixture. A comparison of the absorbance value of the extracted bisphenol with an alkali metal hydroxide equivalents-bisphenol absorbance curve obtained from plotting bisphenol absorbance values with equivalents of alkali metal hydroxide, as shown in the drawing, will establish how far from the (0.5) inflection on the curve the mixture is from stoichiometric balance.

STATEMENT OF THE INVENTION

In the method for making anhydrous alkali metal bisphenol salt by effecting the flash evaporation of water from an aqueous mixture having substantial stoichiometric quantities of alkali metal hydroxide and bisphenol and thereafter using the resulting alkali metal bisphenoxide salt in a displacement reaction for the production of aromatic polyether, whereby the yield of aromatic polyether is substantially reduced if the variance from the stoichiometry of the alkali metal hydroxide or bisphenol initially used in making the bisphenoxide salt exceeds 1.5%, the improvement which comprises (1) adding immiscible organic solvents to the aqueous bisphenoxide salt solution prior to the flash evaporation of water to form a two phase mixture,
(2) determining the stoichiometric variance of alkali metal hydroxide or bisphenol in the aqueous bisphenoxide salt mixture by obtaining the UV absorbance of the bisphenol in the organic phase by spectrographic or chromatographic means, and thereafter finding the equivalents of bisphenol and alkali metal hydroxide in the aqueous bisphenoxide salt mixture by using the aforementioned value of the UV absorbance from the organic phase with a predetermined concentration curve relating bisphenol equivalence in terms of absorbance values and alkali metal hydroxide equivalence, and showing an inflection at substantial stoichiometric equivalence,
(3) adding additional alkali metal hydroxide or bisphenol to the aqueous bisphenoxide salt solution to obtain a bisphenoxide salt solution having substantially a stoichiometric equivalence between alkali metal hydroxide and bisphenol which does not exceed the 1.5% variance, and
(4) effecting the rapid separation of water from the aqueous bisphenoxide salt mixture.

Some of the bisphenoxide salts which can be made by the practice of the present invention are, for example.

$$MO-Z-OM \qquad (1)$$

where Z is a $C_{(6-30)}$ divalent aromatic organic radical and M is an alkali metal ion.

Alkali metals included by M of formula (1) are, for example, sodium, potassium, lithium, etc. Radicals included by Z of formula (1) are, for example

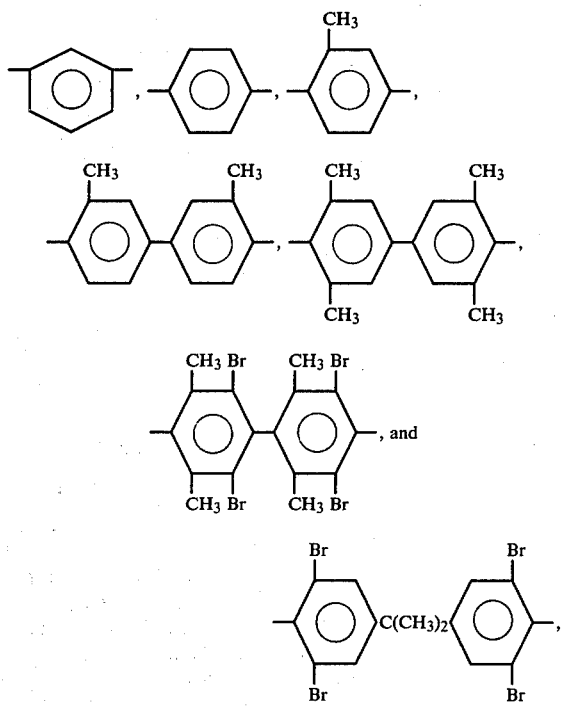

and divalent organic radicals of the general formula,

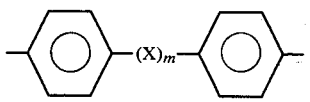

where X is a member selected from the class consisting of divalent radicals of the formulas, $-C_yH_{2y}-$,

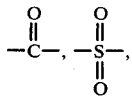

$-O-$ and $-S-$, where m is 0 or 1, and y is a whole number from 1 to 5.

Included by the bisphenols which can be converted to alkali metal salts in accordance with the practice of the invention are, for example,
2,2-bis(2-hydroxyphenyl)propane;
2,4'-dihydroxydiphenylmethane;
bis(2-hydroxyphenyl)methane;
2,2-bis(4-hydroxyphenyl)propane, hereinafter identified as "bisphenol-A" or "BPA";
2(4-hydroxyphenyl)-2(3'-hydroxyphenyl)propane;
1,1-bis(4-hydroxyphenyl)ethane;
1,1-bis(4-hydroxyphenyl)propane;
2,2-bis(4-hydroxyphenyl)pentane;
3,3-bis(4-hydroxyphenyl)pentane;
4,4'-dihydroxybiphenyl;
4,4'-dihydroxy-3,3',5,5'-tetramethylbiphenyl;
2,4'-dihydroxybenzophenone;
4,4'-dihydroxydiphenyl sulfone;
2,4'-dihydroxydiphenyl sulfone;
4,4'-dihydroxydiphenyl sulfoxide;
4,4'-dihydroxydiphenyl sulfide;
hydroquinone;
resorcinol;
3,4'-dihydroxydiphenylmethane;
4,4'-dihyroxybenzophenone; and
4,4'-dihydroxydiphenyl ether.

In order that those skilled in the art will be better able to practice the method of the present invention reference can be made to the drawing.

The drawing shows several points in a curve obtained from standard solutions of toluene containing bisphenol-A, which were extracted from several aqueous disodium salt solutions of bisphenol-A. For example, the following standard solutions were used and the UV absorbance was measured on a Perkin-Elmer UV spectrophotometer at 287 nm.

| Stoichiometry | Absorbance at 287 nm |
|---|---|
| 10% deficient in NaOH (1.80 Eq.) | 1.700 |
| 3% deficient in NaOH (1.94 Eq.) | 0.858 |
| 1.5% deficient in NaOH (1.97 Eq.) | 0.688 |
| Exact Stoichiometry (2.00 Eq.) | 0.515 |
| 1.5% Excess in NaOH (2.03 Eq.) | 0.441 |
| 10% Excess in NaOH (2.20 Eq.) | 0.132 |

An equivalent curve can be obtained by utilizing liquid chromatography or other means for analyzing bisphenol values in the extractive organic solvent used in preparing the graph. The stoichiometry of an unknown aqueous bisphenoxide salt mixture can be readily determined by employing the curve shown by the drawing. For example, if an absorbance of 1.1 is obtained, the aqueous solution contains 1.9 equivalents of alkali metal hydroxide instead of 2.0. An additional 0.1 equivalents or 5% of alkali metal hydroxide, for example NaOH, must be added to balance the stoichiometry. Of particular interest is the linear nature of the graph from 1.8 to 2.0 equivalents of NaOH.

The absorbance of a 98° C. toluene solution which can vary between 5 ml to 100 ml in contact with an equal volume of the aqueous disodium bisphenoxide salt solution at 100° C. having a solids content of about 20% was employed in plotting the curve shown in the drawing using the above standard solutions. The measurements were made at 287 nm (at 287 nm) equals $3.22 \times 10^3$ at 25° C.

In a typical mixture, 18 parts of the disodium salt of bisphenol-A is dissolved in 42 parts of water to give a 30% solution of the biphenoxide salt. The aqueous bisphenoxide salt solution was then diluted with additional water to produce a bisphenoxide salt solution having 20% solids. The aqueous disodium salt of bisphenol-A at 20% solids was then heated for 1 to 2 minutes at 120° C. with stirring for 1-2 minutes. The amount of water in the bisphenoxide salt mixture was then calculated and an equal volume of toluene was added to the aqueous solution. The resulting two phase mixture was then stirred gently for 10 minutes and mixture was then allowed to rest for 5 minutes. The temperature of the mixture at the toluene bisphenoxide salt solution interface was about 100°-101° C. and the mixture was slightly refluxing. An aliquot of the toluene was then carefully removed from the organic phase. The aliquot of the toluene was then diluted with additional toluene until it is completely clear. The UV absorbance of the sample was then be measured with a Perkin-Elmer UV spectrophotometer, employing one centimeter cells and a wave length of 287 nm. The reference cell must contain the toluene from the same bottle used in the extraction method and subsequent dilution. The spectrophotometer should be set at exactly the same wave length each time the measurement is made.

In order that those skilled in the art will be better able to practice the invention, the following example is given by way of illustration and not by way of limitation. All parts are by weight.

EXAMPLE

An aqueous solution of the disodium salt of bisphenol-A having about 20% solids was prepared from 200 parts by weight of bisphenol-A (0.877 mole) and 71.2 parts by weight (1.780 mole) of sodium hydroxide and 954 parts of water. This solution was stirred with an equal volume of toluene at 98° C. for 15 minutes. An aliquot of the toluene solution was then diluted 20 times its volume with fresh toluene and the ultraviolet absorbance of a portion of the resulting toluene solution was measured at a wave length at 287 nm with a Perkin-Elmer model UV spectrophotometer. The absorbance of the toluene solution was found to be 0.441 units. Reference was then made to the previously prepared curve plotted with standard bisphenoxide salt solutions as shown by the drawing. It was determined that the aforementioned aqueous disodium bisphenoxide salt solution was deficient in 3.16 parts by weight (0.013 moles) of bisphenol as it had a 1.5% stoichiometric excess of sodium hydroxide.

The above homogeneous solution of the disodium salt of bisphenol-A was heated to 80° C. under a nitrogen atmosphere. There was then added 866 parts of toluene and the mixture was azeotropically dried using a Dean Stark trap. The formation of a cake of the salt was generally observed near the top of the refluxing liquid during the first hour. This was incorporated into the main portion of the slurry by gently moving it off the walls of the flask with a spatula. Total removal of the last visual traces of water was then accomplished during the following 2-3 hours. This was followed by distillation until there remained 589 parts of toluene in the suspension.

The above suspension was allowed to cool a few degrees. There was then added to the mixture 362 parts of 4-nitrophthalimide, 7.1 part of tetrabutylammonium bromide and 105 parts of benzophenone as an internal standard. The suspension was brought back to reflux to effect the completion of the reaction. There was obtained an 88% yield of 2,2-bis[4-(N-methylphthalimide-4-oxy)phenyl]propane.

The above procedure was repeated, except that additional disodium bisphenoxide salt mixtures were prepared in which the proportions of bisphenol-A and sodium hydroxide were varied. In one instance a disodium bisphenoxide salt was prepared in which there was substantially a stoichiometric equivalence between bisphenol-A and sodium hydroxide as follows:

An aqueous solution of the disodium salt of bisphenol-A having about 20% solid was prepared from 200 parts by weight of bisphenol-A (1 mole) and 72 parts by weight (1.8 mole) of sodium hydroxide and 1,088 parts of water. This solution was stirred with an equal volume of toluene at 98° C. for 15 minutes. An aliquot of the toluene solution was then diluted 20 times its volume with fresh toluene and the ultraviolet absorbance of a portion of the resulting toluene solution was measured at a wave length at 287 nm with a Perkin-Elmer model UV spectrophotometer. The absorbance of the toluene solution was found to be 1.70 units. Reference was then made to the previously prepared curve plotted with standard bisphenoxide salt solution. It was determined that the aforementioned aqueous disodium bisphenoxide salt solution was deficient in 8 parts by weight (0.2 moles) of sodium hydroxide. There was then added 8 parts by weight of sodium hydroxide to the aqueous solution of the disodium salt of bisphenol-A. The resulting solution was again stirred with an equal volume of toluene and measured for its UV absorbance, based on extractive bisphenol-A. It was found that the resulting bisphenoxide salt solution provided an absorbance measurement in the toluene phase of 0.495 absorbance units. This indicated that a substantially stoichiometric balance between bisphenol-A and sodium hydroxide in the aqueous disodium bisphenoxide salt solution.

The following results show the yield of 2,2-bis[4-(N-methylphthalimide-4-oxy)phenyl]-propane, "bisimide yield" when substantially stoichiometric amounts of the disodium bisphenoxide salts having either a 1.5% to 3% excess of bisphenol-A or sodium hydroxide, as well as substantial stoichiometric equivalence thereof were reacted with 4-nitrophthalimide as described above.

| Bisphenoxide Salt Stoichiometric | Bisimide Yield (%) |
| --- | --- |
| 1.5% Excess BPA | 93 |
| 1.5% Excess NaOH | 88 |
| 3.0% Excess BPA | 62 |
| 3.0% Excess NaOH | 70 |
| Exact Balance | 99 |

The above results show that there is a significant reduction in the yield of bisimide when the disodium bisphenoxide salt is used in bisimide synthesis which exceeds the 1.5% stoichiometric variance, while optimum bisimide yield is obtained with disodium bisphenoxide salt at substantial stoichiometric equivalence.

Although the above example is directed to only a few of the very many variables to which the method of the present invention can be applied it should be understood that the present invention is directed to a method of making a much broader variety of bisphenoxide salts which are shown in the description preceding this example.

What we claim as new and desire to secure by Letters Patent of the United States is:

1. A method for making anhydrous alkali metal bisphenol salt as the result of the reaction between bisphenol and an alkali metal hydroxide, where the proportions of the bisphenol or alkali metal hydroxide in the anhydrous alkali metal bisphenol salt do not exceed a 1.5% variance from stoichiometry, which comprises
    (1) making an aqueous alkali metal bisphenol salt solution from substantially equivalent amounts of bisphenol and alkali metal hydroxide,
    (2) contacting at least a portion of the aqueous solution of (1) with an immiscible organic solvent to produce a two phase mixture,
    (3) obtaining a UV absorbance value of the organic phase of (2),
    (4) applying the absorbance value found in (3) in a predetermined concentration curve showing equivalents of alkali metal hydroxide against UV absorbance values and calculating alkali metal hydroxide variance from stoichiometry,
    (5) adding additional alkali metal hydroxide or bisphenol to the aqueous bisphenoxide salt solution of (1) to obtain an alkali metal bisphenoxide salt mixture having a substantial stoichiometric relation between alkali metal hydroxide and bisphenol, and
    (6) effecting the separation of water from the resulting aqueous bisphenoxide salt mixture of (5) to produce the anhydrous alkali metal bisphenoxide salt within a 1.5% stoichiometric relationship between bisphenol and alkali metal hydroxide.

2. A method in accordance with claim 1, where the bisphenol is bisphenol-A.

3. A method in accordance with claim 1, where the immiscible organic solvent is toluene.

4. A method in accordance with claim 1, where the alkali metal hydroxide is sodium hydroxide.

5. A method in accordance with claim 1, where the water is removed by azeotropic distillation.

6. A method in accordance with claim 1, where the water is removed by azeotropic distillation with toluene.

* * * * *